United States Patent
Hwang et al.

(10) Patent No.: US 9,486,179 B2
(45) Date of Patent: Nov. 8, 2016

(54) MULTILAYERED PHANTOM TISSUE TEST STRUCTURE AND FABRICATION PROCESS

(71) Applicants: Jeeseong Hwang, Gaithersburg, MD (US); Christopher Stafford, Ijamsville, MD (US); Robert Chang, Gaithersburg, MD (US)

(72) Inventors: Jeeseong Hwang, Gaithersburg, MD (US); Christopher Stafford, Ijamsville, MD (US); Robert Chang, Gaithersburg, MD (US)

(73) Assignee: The United States of America, as represented by the Secretary of Commerce The National Institute of Standards and Technology, Washington, DC (US)

( * ) Notice: Subject to any disclaimer, the term of this patent is extended or adjusted under 35 U.S.C. 154(b) by 358 days.

(21) Appl. No.: 14/019,128

(22) Filed: Sep. 5, 2013

(65) Prior Publication Data
US 2014/0072770 A1    Mar. 13, 2014

Related U.S. Application Data

(63) Continuation-in-part of application No. 13/733,612, filed on Jan. 3, 2013, now abandoned.

(60) Provisional application No. 61/582,858, filed on Jan. 4, 2012.

(51) Int. Cl.
*A61B 6/00* (2006.01)
*B32B 3/26* (2006.01)
*B32B 38/10* (2006.01)
*A61B 5/00* (2006.01)
*G01B 9/02* (2006.01)

(52) U.S. Cl.
CPC ............ *A61B 6/583* (2013.01); *A61B 5/0066* (2013.01); *A61B 5/7221* (2013.01); *B32B 3/263* (2013.01); *B32B 38/10* (2013.01); *G01B 9/02072* (2013.04); *G01B 9/02091* (2013.01); *Y10T 428/24612* (2015.01)

(58) Field of Classification Search
CPC .. A61B 6/583; B32B 3/263; G01B 9/02091; Y10T 428/24612
See application file for complete search history.

(56) References Cited

U.S. PATENT DOCUMENTS

2009/0075391 A1* 3/2009 Fulghum, Jr. ...... A61B 1/00165
                                                                  436/164
2011/0062318 A1* 3/2011 Bisaillon .............. G09B 23/285
                                                                  250/252.1

OTHER PUBLICATIONS

Curatolo, Andrea; Brendan F. Kennedy, and David D. Sampson. "Structured three-dimensional optical phantom for optical coherence tomograhy." Optics Express. vol. 19, No. 20. pp. 19480-19485. Sep. 26, 2011.*

* cited by examiner

*Primary Examiner* — Nancy Johnson
(74) *Attorney, Agent, or Firm* — AbsoluteTechnologyLawGroup, LLC

(57) ABSTRACT

A multilayered optical tissue phantom fabrication approach and inherently produced test target structure which address the issues of of optical conformity known in the art by controlling the formation of micrometer scale monolayers embedded with light-scattering microspheres.

20 Claims, 11 Drawing Sheets

MULTILAYERED PHANTOM TISSUE TEST STRUCTURE AND FABRICATION PROCESS

CROSS-REFERENCE TO RELATED APPLICATIONS

This application is a continuation-in-part of U.S. Non-Provisional application Ser. No. 13/733,612 filed on Jan. 3, 2013, which claimed priority to U.S. Provisional Application No. 61/582,858.

STATEMENT OF GOVERNMENT INTEREST

The invention described herein was made by employees of the United States Government and may be manufactured and used by or for the Government of the United States of America for governmental purposes without the payment of any royalties thereon or therefor.

FIELD OF INVENTION

The present invention relates to calibration of imaging devices and in particular to a method for fabrication of a phantom test structure and the unique structure inherently created by the method disclosed.

BACKGROUND

Figure 1A:
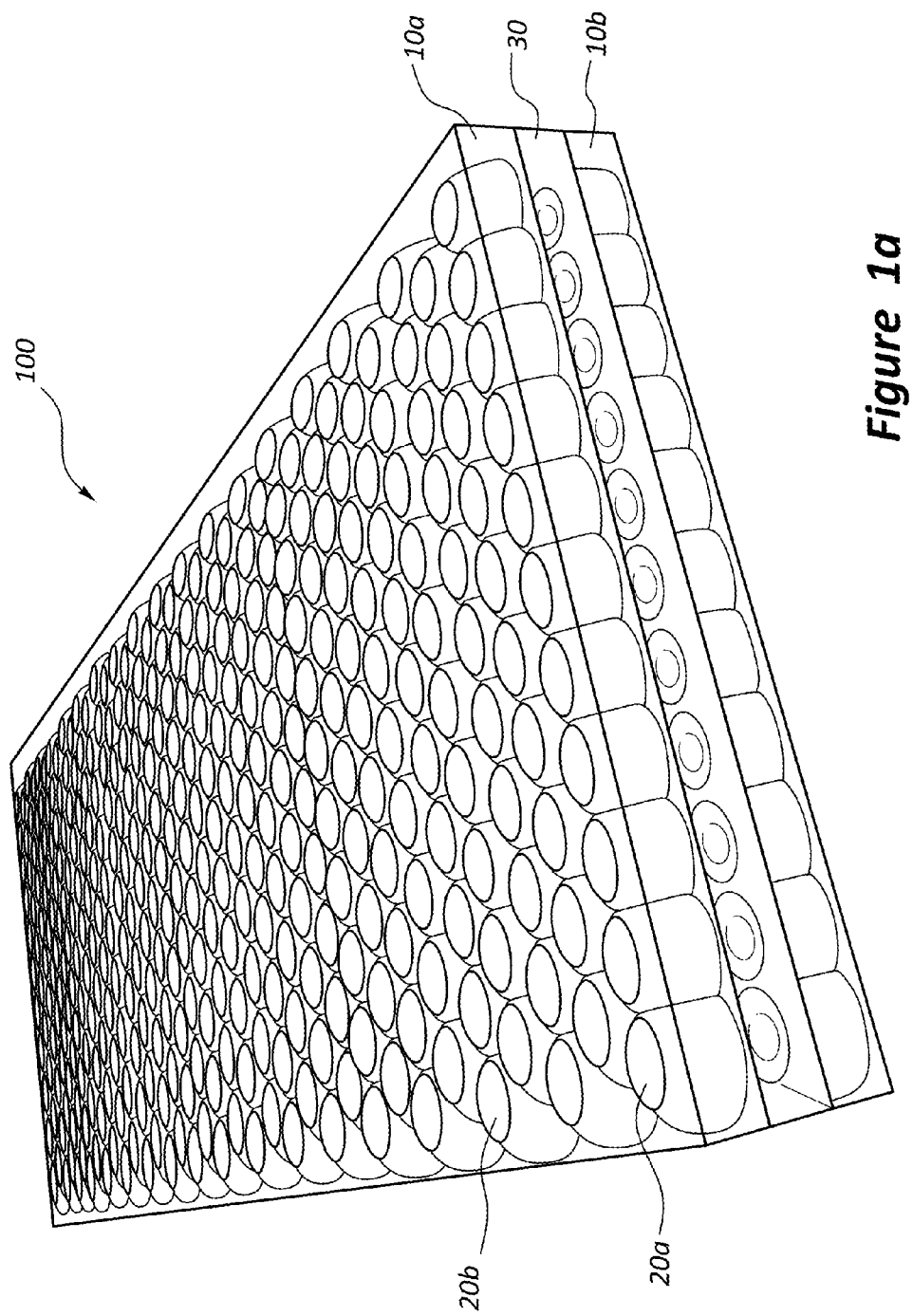
FIGS. 1a through 1d illustrate alternate views of an exemplary embodiment of a multi-layered phantom test target structure in an optical tissue phantom test structure.
Figure 1B:
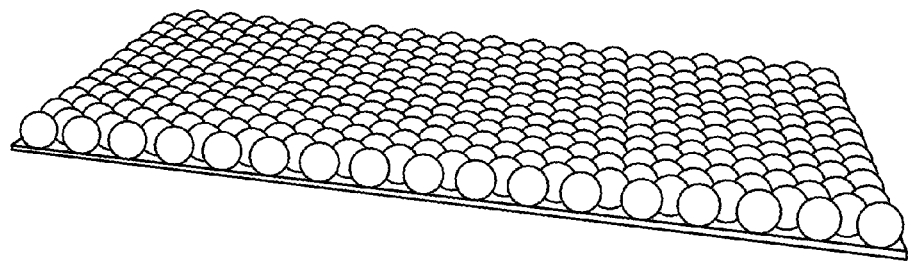
Figure 1C:
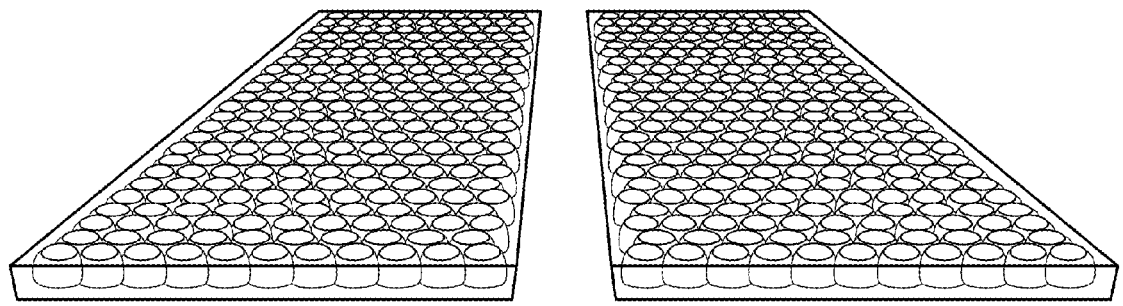
Figure 1D:
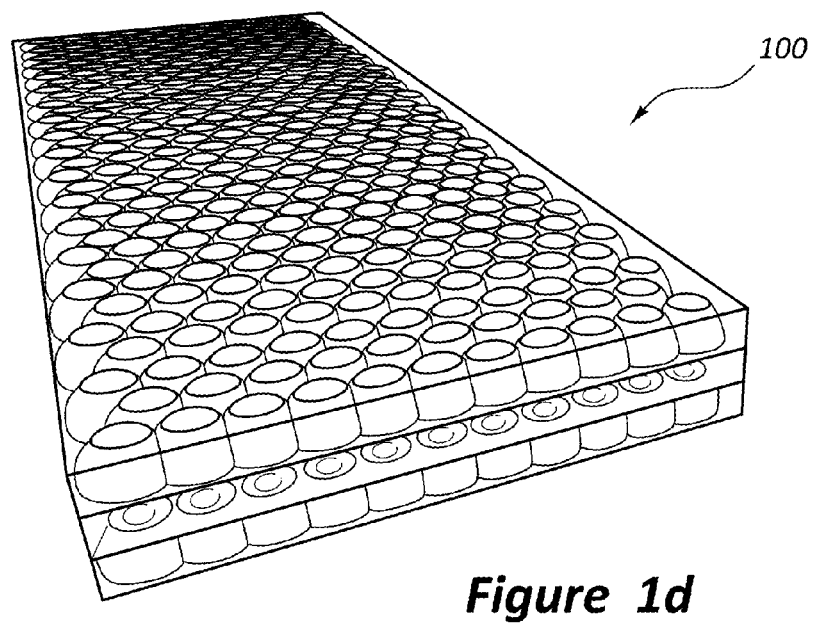

The National Institute of Standards and Technology (NIST) is a non-regulatory agency of the United States Department of Commerce which exists to promote scientific advancement of science through the use of measurement standards. Consistent with its mission, NIST has been at the forefront of research for developing "phantom" test objects to ensure the reliability of rapidly advancing imaging technologies.

Medical imaging devices and systems must be calibrated to ensure uniformity and reliability of test results. Calibration is necessary to ensure the highest possible degree of accuracy for all data obtained through imaging. Calibration may require the use of a sample or an object on which testing or imaging can be performed. With respect to human tissue and fragile or volatile test materials, it is useful to have a structure which may emulate the physical characteristics of the material on which imaging is to be performed for purposes of calibrating the imaging instruments.

A "phantom" test target is an object that simulates the structure of the tissue or other materials for which an imaging device or system is used for a system under test. The phantom test target is created to replicate structural characteristics of the tissue or the other materials for which the imaging device is used. Phantom test targets are used for calibration inter-laboratory comparison, and standardization of imaging platforms. They are also used for the validation of physical models and simulations to quantitatively interpret the image data.

There are more than 30 imaging modalities that currently utilize tissue phantoms. The phantom test targets ensure the reliability of medical imaging systems and scientifically advance the levels of accuracy that medical imaging technologies can achieve.

The phantom test targets are scanned or imaged by an imaging system under test to calibrate the performance of the imaging devices known in the art. The phantom test targets can mitigate the need to have the tissue or the other materials available for calibration (e.g., a tissue donor, live subject, cadaver or samples of organic or inorganic material).

Optical coherence tomography (OCT) is an imaging technology that uses near-infrared light. OCT captures micrometer-resolution, three-dimensional images from within the tissue or the other materials. The use of relatively long wavelength light allows it to penetrate into the tissue or the other materials. The materials imaged are sometimes referred to as light scattering medium.

Light scattering is the deflection of light due to irregularities in the propagation medium or in the interface between two media.

Scattering of light depends on the wavelength or frequency of the light being scattered. Visible light has wavelength on the order of a micrometer.

OCT can achieve sub-micrometer image resolution by using very wide-spectrum sources emitting over a ~100 nm wavelength range. Frequency-domain optical coherence tomography is a form of OCT, which reduces signal-to-noise ratios, permitting faster signal acquisition. Another imaging modality at higher resolutions for in vivo applications is confocal microscopy, which enables the visualization of superficial layers at a depth of up to a few hundred micrometers with sub-micrometer resolution.

OCT systems have widespread commercial applicability for art and material conservation and diagnostic medicine. For example, OCT is frequently used in ophthalmology where it can be used to obtain detailed images from within the retina. OCT is also used in oncology and in interventional cardiology to help diagnose coronary artery disease.

To produce traceable and verifiable results, a tissue phantom must have well-controlled optical properties (refractive index, scattering coefficient, anisotropy factor, and absorption coefficient). Tissue phantoms are used to measure instrument characteristics such as point spread functions (PSFs) for the evaluation of lateral and axial resolutions, spectral responsivity for quantitative analyses of fluorescence and wavelength-dependent scattering, and detection sensitivity and dynamic range for tissue type-dependent optical densities and molecular concentration of target and image-contrast probes.

Phantoms made from polymeric materials are known in the art. Polymers are routinely used because of their general biocompatibility. Polymers also have the ability to form stable matrices that allow easy inclusion of various entities (e.g. polymer microparticles, cellular constituents, dyes), and tunability of absorption and scattering characteristics.

However, there are several problems known in the art with respect to the fabrication of tissue phantoms. There is no existing process for forming standard uniform tissue phantoms for accurate optical device inter-comparison.

One problem known in the art is the lack of uniformity in the use of phantom fabrication materials.

Calibration standards are necessary for both lateral and axial resolution. The United States Air Force (USAF) provides a test chart for lateral resolution calibration, using the widely accepted MIL-STO-I 50A standard. The standards provides a pattern of alternating dark/bright line pairs of decreasing periodicity with dimensions ranging from 4 µm to 1 mm to test the quality of the optical system. However, this standard is inapplicable to axial resolution.

Axial resolution calibration is particularly important for depth-resolving optical systems such as OCT and confocal microscopy. There is currently no widely accepted standard for axial resolution in the scientific community.

A standard, replicable phantom tissue test target is particularly needed in the field of ophthalmology. OCT is used to acquire optical biopsies of the retinal layers. Highly accurate quantitative thickness measurements of nerve fiber layer along with other intra-retinal layers facilitate diagnosis of conditions such as age-related macular degeneration, diabetic retinopathy, epi-retinal membranes, and glaucoma.

It is desirable to have a phantom test structure to have uniformity of surfaces and interfaces that produce light scattering. This characteristic is called optical uniformity. Optical uniformity greatly enhances the precision and accuracy of calibration.

It is desirable to have a phantom tissue test target which achieves optical uniformity and advances OCT calibration and diagnostic science.

TERMS OF ART

As used herein, the term "axial layer position" means the position of a microsphere relative to the surface of a monolayer which determines the surface profile layer.

As used herein, the term "bulk" means multiple.

As used herein, the term "calibration" means testing of any metric.

As used herein, the term "light-scattering" refers to the phenomena by which a physical deviation in a medium or surface deflects light in a detectable manner.

As used herein, the term "microsphere" means contoured or spherical particles with diameters measured in micrometer range. Microspheres may be hollow or solid and of uniform and varying sizes.

As used herein, the term "modified glass substrate" means a glass substrate that has been washed, coated or chemically treated with a solution or which has been heated or cooled chemically to alter the electrical or other properties of its surface, such a polyelectrolyte multilayer (PEM).

As used herein, the term "monolayers" means a layer or substrate of any solid, liquid or gas material which may or may not include or be in contact with microspheres.

As used herein, the term "OCT" or "optical coherent tomography" means any imaging device system capable of being calibrated using a phantom test target, and is not limited to technologies specifically referred to by this acronym.

As used herein, the term "optical uniformity" or "optical conformity" means the process or characteristic of having replicable light diffusing characteristics with minimal interference from surface irregularities.

As used herein, the term "particle flux" means particle movement within a meniscus or on a surface of a substrate.

As used herein, the term "PEM" means polyelectrolyte multilayer.

As used herein, the term "phantom" means a structure which emulates light scattering characteristics of organic or inorganic material which is tested or device system under test.

As used herein, the term "plurality" means two or more.

As used herein, the term "PDMS" or "PDMS elastomer" means a silicone-oil-based polymer having viscoelastic properties, and includes other materials.

As used herein, the term "polymer" means a polymer having viscoelastic properties.

As used herein, the term "polystyrene" means a synthetic resin that is a polymer of styrene.

As used herein, the term "PS microspheres" means microspheres made from polystyrene.

As used herein, the term "test measurement data" means any data which can be obtained using an optical imaging instrument.

As used herein, the term "test target" means a calibrated testing structure with structural properties that are inherently created by a method which uses data values.

As used herein, the term "viscoelastic" refers to the properties of materials (e.g., viscous and elastic responses) or are an intermediate of both liquids and solids in character.

SUMMARY OF THE INVENTION

The invention described herein is a multilayer phantom test target that is unique and is inherently produced by the fabrication method disclosed.

The present invention is a process which inherently creates specific phantom test structures that serve as independent test targets (devices) for calibrating the axial resolution of optical coherent tomography (OCT) devices. The structure also creates contrast in scattering measurements obtained by depth-resolving OCT. The structures formed during the process are monolayers of light-scattering microspheres with interspersed layers of transparent polymer. A dense monolayer assembly of monodispersed microspheres is achieved via a combined methodology of polyelectrolyte multilayers (PEMs) for particle-substrate binding and convective particle flux for two-dimensional crystal array formation on a glass substrate. The microspheres formation is then transferred from the chemically treated glass substrate onto a polymer monolayer while preserving the relative coplanar axial positioning within monolayer. Phantom test object properties can be varied, including the dimensions of microspheres, the thickness of the intervening polymer, and the spatial frequencies of the microsphere layer in the axial dimension. Phantom test object dimensions are formed independently of the optical systems under test to enable precise spatial calibration and independent validation.

DETAILED DESCRIPTION OF THE INVENTION

For the purpose of promoting an understanding of the present invention, references are made in the text to exemplary embodiments of a phantom test structure 100, only some of which are described herein. It should be understood that no limitations on the scope of the invention are intended by describing these exemplary embodiments. One of ordinary skill in the art will readily appreciate that alternate but functionally equivalent steps and components may be used. The inclusion of additional elements may be deemed readily apparent and obvious to one of ordinary skill in the art. Specific elements disclosed herein are not to be interpreted as limiting, but rather as a basis for the claims and as a representative basis for teaching one of ordinary skill in the art to employ the present invention.

It should be understood that the drawings are not necessarily to scale; instead emphasis has been placed upon illustrating the principles of the invention. In addition, in the embodiments depicted herein, like reference numerals in the various drawings refer to identical or near identical structural elements.

Moreover, the terms "substantially" or "approximately" as used herein may be applied to modify any quantitative representation that could permissibly vary without resulting in a change in the basic function to which it is related.

FIG. 1a through 1d illustrate an exemplary embodiment of a phantom test structure 100, which shows an assembly of monolayers 10a, 10b, constructed from light-scattering polystyrene (PS) microspheres 20a, 20b, and surrounded by a polydimethylsiloxane (PDMS) elastomer layer 30. The exemplary embodiment shown is a multilayered optical tissue phantom test target structure.

By varying the dimensions and axial position of embedded microspheres 10a, 10b, and the thickness of monolayers 20a, 20b different spatial frequencies are replicated in the axial dimension of the phantom. These frequencies can provide a standardized approach to determine the axial contrast transfer function for a wide range of quantitative measurements achieved by an OCT imaging system, and can adapt to incorporate measurements that may be achieved by any OCT imaging tool developed. Phantom test target structure 100 can achieve highly precise spatial calibration which accommodates all types of measurements that can be achieved by the use of OCT technology.

In the embodiment shown, phantom test target structure 100 may be used for precise spatial positioning to periodically check measurement accuracy for quantitative axial information needed to measure tissue thicknesses (e.g., quantifying morphological aberrations for early disease detection.) The exemplary embodiment shown may incorporate microspheres of various known sizes and refractive indices at precise axial positions.

In various embodiments, phantom test target structure 100 may incorporate layer dimensions defined by microsphere size selection and tunable interparticle spacing between scattering layers. Phantom test structure 100 enables scattering tissue to be modeled with Mie theory.

Phantom test target structure 100 is a stable, single portable unit without discernible layer interfaces.

In various embodiments, phantom test target structure 100 may be multilayered to achieve a particular axial resolution and contrast. For example, the exemplary phantom test target structure 100 consists of alternating reflective (or scattering) and transparent monolayers 10a, 10b with known thickness for each layer and the periodicity of the repeating layers.

In the scattering-based depth-resolving imaging modalities, such as OCT, the reflective layers should also have homogeneous scattering characteristics (i.e., optical conformity) to appear uniformly bright in the image much like a metal film on glass would produce a laterally uniform brightness.

A set of multilayered phantoms may be fabricated to cover spatial frequencies expected from the theoretical axial resolution of OCT, as estimated from the OCT illumination source coherence length.

The optically conformed phantom test target structure 100 is an inherent structure produced exclusively by the method disclosed herein. The method and inherent structures produced address the problem of optical conformity of refractive surfaces known in the art. An optically conformed surface is one which has minimal irregularities which may alter the reflective qualities of the surface of a phantom test target structure.

In various embodiments, phantom test target structure 100 may be fabricated to replicate attributes of axial resolution and contrast in scattering-based measurements (e.g., as would be made in retinal thickness measurements).

The bottom-up method determines the inherent characteristics of each microsphere assembly of a monolayer of polystyrene (PS) microspheres and transfers them into a polydimethylsiloxane (PDMS) elastomer to produce phantom structures.

In various embodiments, phantom dimensions may be independently measured in bulk using surface interferometric techniques known in the art. Bulk testing can facilitate a repeatable determination of sub-surface particle distributions within the polymeric material.

Fabrication of phantom test target structure 100 can be accomplished by various physical mechanisms. Varying techniques may be used to collect and organize the microspheres and then bind the structure formed onto a substrate material via concentration of monodispersed spherical microspheres. For example, collection can be achieved by simple sedimentation methods, but can also be directed and organized by convection and capillarity, or driven by external fields.

The charged microspheres 20a, 20b are then coated with a polydimethylsiloxane (PDMS) host polymer to form monolayers 10a, 10b. PDMS possesses viscoelastic properties that facilitate both molecular contact with the substrate and exhibit strong resistance to stress thresholds during delamination or debonding. Advantages of both the liquid and the solid character that determine the debonding process is integral to an adhesive's performance.

PDMS is a cross-linked polymer, PDMS, which consists of a silicone oil base along with a curing agent that formed chemical cross-links between the polymer chains. Without adding any curing agent, the PDMS is a Newtonian liquid. When a curing agent is added, increments of cross-links in the polymer backbone are formed and the material became viscoelastic. Adding about 10% of a curing agent yields the fully cured elastic solid. PDMS is an elastomer with a very low Young modulus of about lMPa, and very low surface energy of 22.7 mJ m$^{-2}$. These two properties together allow a cured PDMS construct to reversibly stick to itself or other solids by means of van der Waals forces. This rather weak bonding (the adhesion work of PDMS and glass is 0.1 to 0.2 J m$^{-2}$) is suitable for the phantom fabrication in which small pressures (~35 kPa) are enough to delaminate the PDMS layer from the glass substrate 40 without rendering significant defects or blistering.

Figure 2:
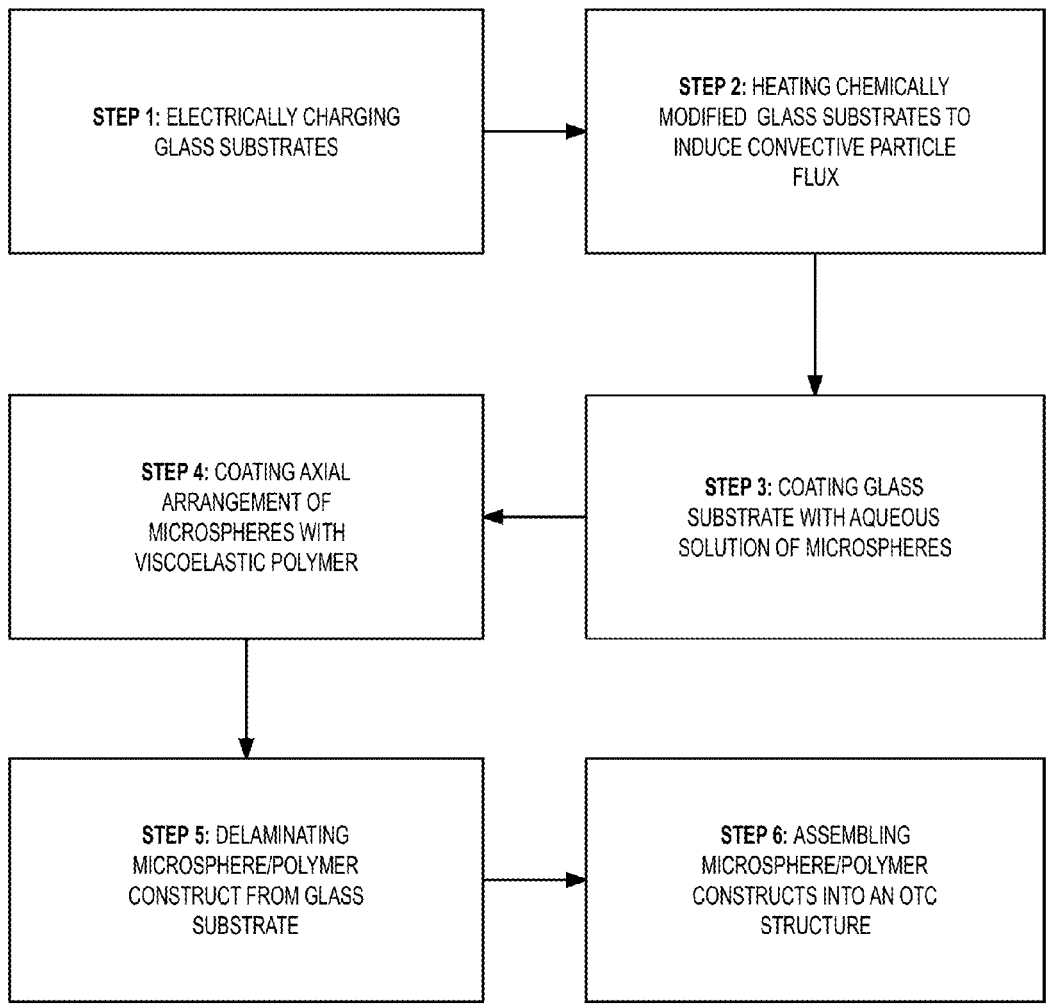
FIG. 2 is a flow chart for an exemplary method for fabrication of multi-layered phantom test target structures.

FIG. 2 illustrates an exemplary embodiment for producing a multilayer phantom test target structure 100 as described herein, and the phantom test target structure disclosed herein is inherently produced by this method.

The method may be used for the characterization of axial resolution and contrast in scattering-based measurements as would be made in retinal thickness measurements. By varying the dimensions of the embedded microspheres and the thickness of intervening polymer layers, different spatial frequencies are replicated in the axial dimension of the phantom. Furthermore, these frequencies can provide a standardized approach to determine the axial contrast transfer function for the quantitative application in an OCT imaging system. For precise spatial calibration, bulk phantom dimensions were independently measured using a surface interferometric technique and confocal microscopy. Such a test system enabled a more accurate and repeatable determination of sub-surface particle distributions within the polymeric material and interparticle polymer thickness.

In Step 1, glass substrates are plasma treated to confer a uniform negative charge. This allows the modified glass substrate to serve as a uniformly charged surface to introduce a bed of alternating charged solutions to the glass substrate.

In one exemplary embodiment, a plasma-treated glass substrate is successively dip-coated with several alternating charged bilayers of polyelectrolytes. The charged bilayers are formed using layer-by-layer (LBL) assembly from aqueous solutions of the polycation polyallylamine hydrochloride (PAH) and the polyanion polysodium 4-styrene sulfonate (PSS) for 15 minutes each with successive 1-minute washings with deionized water (DI) in between.

In Step 2, the chemically charged glass substrate is coated with an aqueous solution of negatively charged polystyrene microspheres.

In Step 3, optionally, the chemically modified glass substrate that is coated with the meniscus of microspheres may be heated to facilitate convective particle flux to actively form an ordered monolayer array of microsphere.

In this embodiment, water evaporation may act as a passive mechanism to produce convective particle flux to form an ordered arrangement of microspheres. Various embodiments may include a step of pre-heating the modified glass substrate that is coated with the microsphere particle suspension, thus causing the two dimensional monolayer array or crystals to move moving meniscus of the evaporating particle suspension. A capillary force-driven crystallization process occurs as the particles carried by the flux of liquid towards the drying front are concentrated and incorporated in the transition region between the meniscus and the drying crystal array of microspheres.

In Step 4, the axial arrangement of microspheres is preserved during the process of polymer flow coating. It is critical that the host polymer have viscoelastic properties that enable enhanced molecular contact with the substrate and strong resistance to stress thresholds during delamination or debonding. The balance between the liquid and the solid character is critical to the debonding process. The embodiment shown utilizes a cross-linked polymer, polydimethylsiloxane (PDMS), which consists of a silicone oil base along with an optional curing agent that formed chemical cross-links between the polymer chains. In various embodiments, 5-20% of curing agent may be added to tune to mechanical elastic modulus of the cured polymer.

In Step 5, the microspheres and monolayer are delaminated from the glass substrate. When the microspheres are delaminated from the glass substrate, the particles are transferred into the PDMS elastomer as a monolayer of PS particles and is axially positioned subjacent to the polymer surface.

In Step 6, the layers are arranged to form the multi-layer test target structure. The exemplary method utilizes surface profilometer with a 5× objective and 640×480 pixel camera, capable of measuring step height changes over a range of 50 nm to 1 mm, and is used to measure surface profiles for the microsphere-embedded polymer construct and thicknesses of the successively layered structure fabricated using the multilayer buildup process. The surface profilometer was calibrated to a known NIST-traceable step height standard (Model #SHS-1.8QC, Serial #10783-08-16). Relative axial positioning of the microspheres within the host elastomer were obtained by taking an XZ scan with a laser-scanning confocal Leica TCS SP5 microscope (Leica, Germany) using a 60×0.5 oil-immersion objective.

In one exemplary method embodiment, phantom samples may be imaged with both Fourier domain OCT (FDOCT) and time domain OCT (TDOCT) systems. The FDOCT system may be operated at a center wavelength of 855 nm with 56 nm full-width at the half-maximum (FWHM) spectral bandwidth, yielding an approximate FWHM coherence length of 6 µm. The TDOCT system, based on an all-fiber common-path interferometer, operated at a center wavelength of 1315 nm with 53 nm FWHM spectral bandwidth, yielding a ≈15 µm FWHM coherence length. 1 mm wide 8-scans were captured from each phantom, and the A-scans in each image were averaged together for quantitative assessment of resolution via the intensity modulation generated by layers (e.g., two bright layers separated by a dark layer).

Several parameters are critical to the method disclosed in FIG. 2.

For example in Step 1, a process to produce a tightly packed PS microsphere coating on a glass substrate first involves the LBL deposition of microspheres (electrostatic polyelectrolytes). A key parameter for polyelectrolyte suspensions involving dissociated electrolytes is the Debye or screening length scale beyond which the effect of the electrostatic charge no longer contributes to the surface attachment, as the counter-ions cluster near opposing charged surfaces to effectively screen the charge of a charged surface or polymer. This Debye length is given by:

$$K^{-1} = \left(4\pi N_A L_b C_p \frac{l}{\xi}\right)^{-0.5}$$

for polyelectrolyte solutions without any added salt. $N_A$ is Avagadro's number, $L_b$ is the Bjerrum length, $C_p$ is the polyelectrolyte concentration, and $\xi$ is the linear charge density of the polyelectrolyte. The Bjerrum length is a parameter which describes the length scale at which the thermal energy equals the electrostatic potential energy between two elementary charges and is given by:

$$L_b = \frac{e^2}{4\pi\varepsilon kT}$$

where is e the elementary charge, $\in$ is the dielectric constant of the medium, k is the Boltzmann constant, and T is the absolute temperature. Significant charge separation can only occur when the distance between two opposite charges is greater than these length scales such that both electrostatic screening and thermal energy inhibit charge recombination. In the presence of salt in the polyelectrolyte solution, since the Debye length varies as follows:

$$K^2 \sim c + 2\approx_s^2 c_s$$

where $\approx_s$ and $c_s$ are the valence and concentration, respectively, of the salt counter-ions and c is the polymer concentration where the addition of salt decreases the Debye length due to enhanced screening from the additional charges.

Polyelectrolytes are generally more rigid than uncharged polymers because the entropic driving force toward coiling and random chain conformations is inhibited by the intramolecular electrostatic repulsion of the charges along the chain backbone resulting in more correlated packing of the intermolecular polymer backbone. A measure of this rigidity is the persistence length $L_p$, i.e. the length over which correlations in the direction of the backbone (at a given starting point) are lost or an essential measure of how long it takes for the chain to turn around. This length scale is given by the characteristic ratio, $C_\infty$ and the bond length, L as follows:

$$L_p = \frac{L}{2}(C_\infty + 1) L_p = \frac{L}{2}(C_\infty + 1)$$

It is thus inferred that the polyelectrolyte chain conformation becomes more rod-like or stiffer with a concomitant increase in the charge density along the chain. When the concentration of counter-ion in a polyelectrolyte solution is increased, counter-ion condensation effectively reduces the charge density along the backbone, resulting in the increase of the mean spacing, b, between charges on the chain, then so does the Debye length according to the following equation:

$$\xi = \frac{L_b}{b}$$

Since the Debye length is linearly correlated with the persistence length, $L_b$, it increases as well and results in a stretched chain at higher charge densities. When $\xi$ is unity, the charge spacing equals the Bjerrum length and the entropic driving force towards coiling equals the electrostatic driving force toward chain stretching. When charge density increases further, polyelectrolyte chain stretching predominates over coiling which may result in a uniformly spaced charge distribution and lesser extent of interdigitation with an oppositely charged polyelectrolyte chain. For the polymer-microsphere system, the NaCl salt concentrations were varied to identify the optimal regimen for maximal particle-substrate binding yet mitigate the extent by which screening salt counter-ions interfere with the subsequent electrostatic absorption of microspheres to the modified glass substrate and the charge-density dependent stretching of the polyelectrolyte chain conformation.

FIGS. 3a through 3b illustrate various structures produced by alternate embodiments for fabricating multi-layered test target structures.

FIG. 3a illustrates a structural embodiment that is produced when a PDMS elastomer formulation approximately 1 mm thick is cast onto monolayer, after the microspheres absorbed onto the glass substrate.

Figure 3:
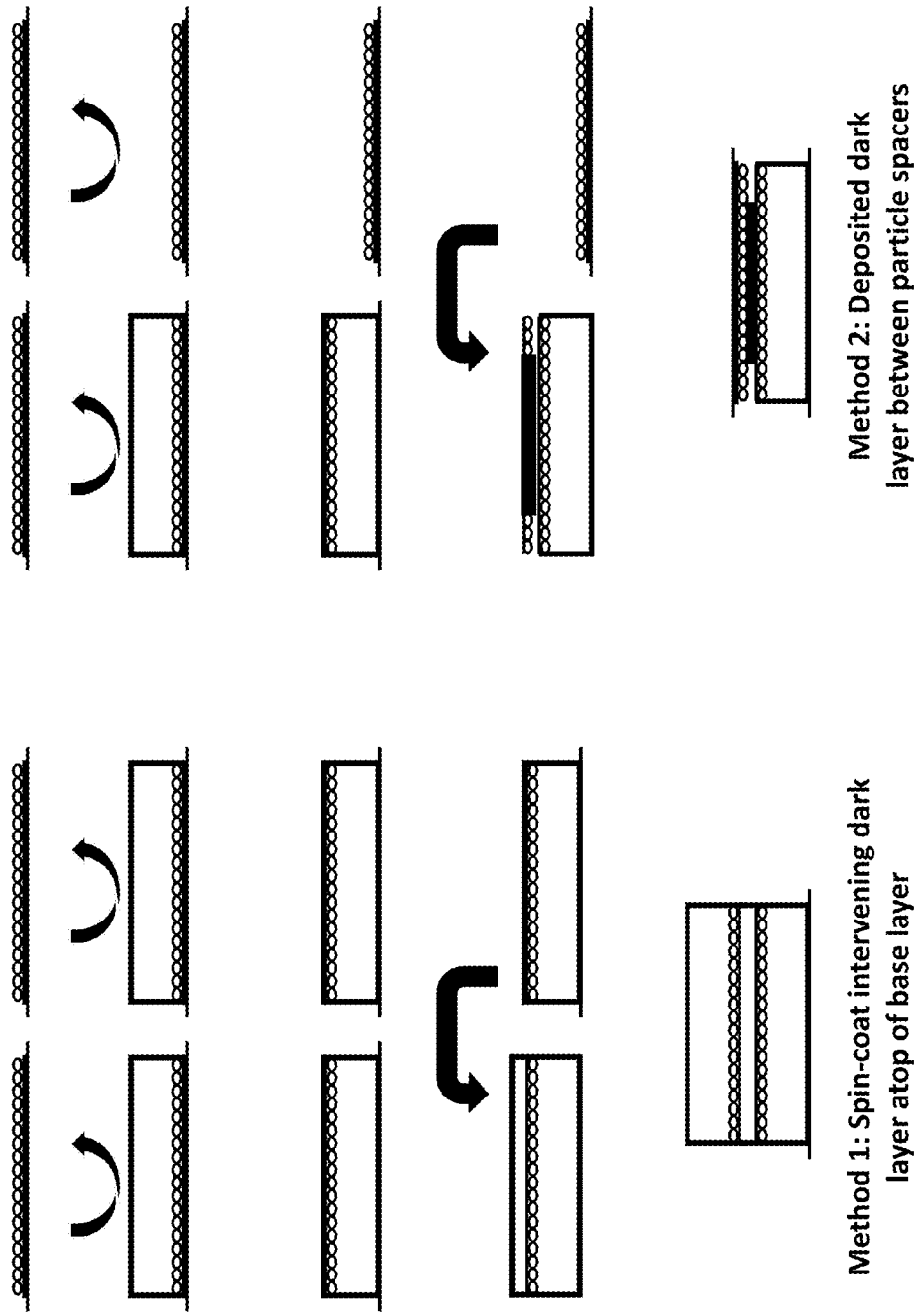
FIGS. 3a through 3b illustrate the structure of phantom test targets inherently produced by various embodiments of the method disclosed.

NOTE: We have updated FIG. 3 at the end of this document for improved clarity of the fabrication methods. FIG. 3b represents an alternate embodiment for FIG. 3a for fabricating the multi-layered test target structure. In FIG. 3a, the intervening layer is spin-coated. In FIG. 3b, particle spacers are positioned at the lateral ends atop the base layer and polymer is flow-coated between the particle spacers. A glass substrate with adherent microspheres is then placed atop the spacer and intervening polymer layer.

Figure 4:
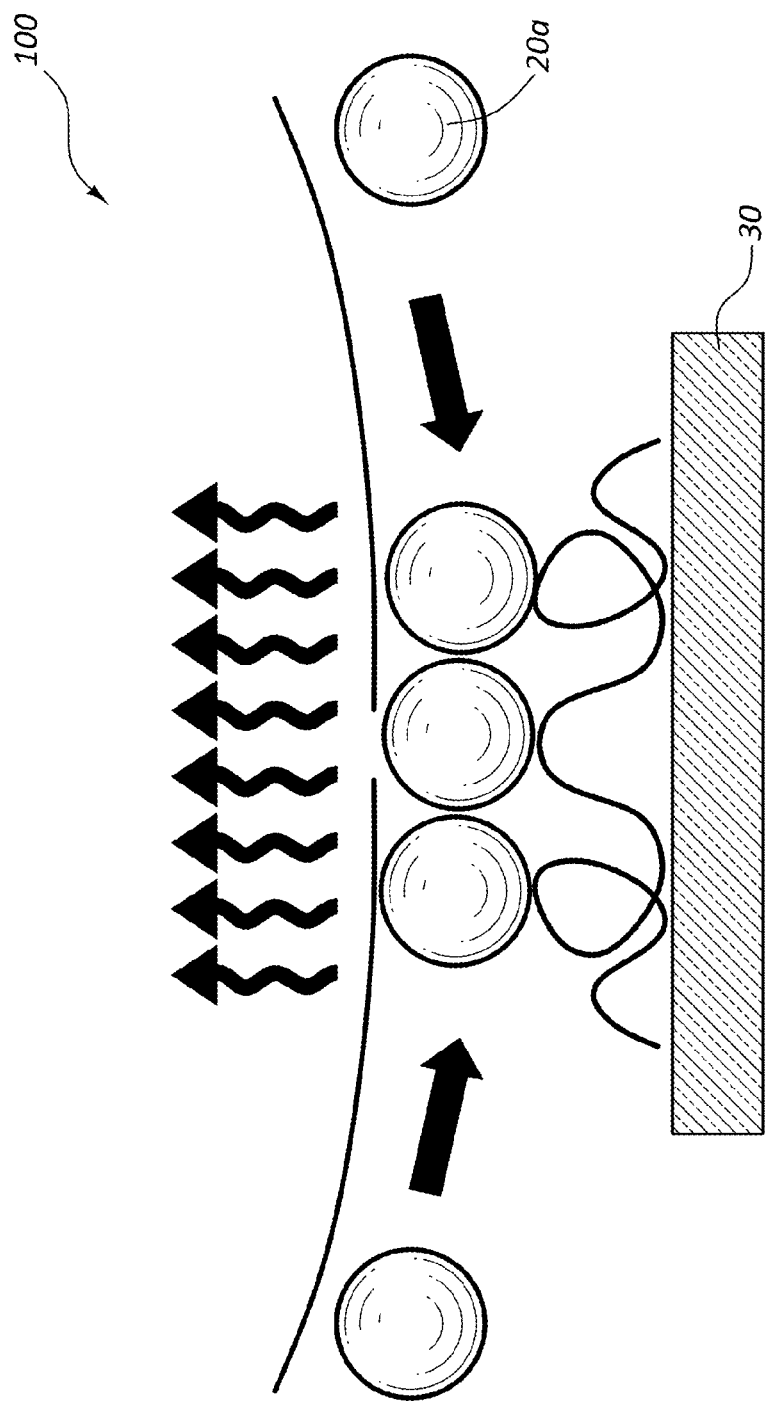
FIG. 4 illustrates the optional step of heating a glass substrate to induce convective particle flux.

FIG. 4 illustrates the optional step of heating a glass substrate to induce convective particle flux.

Figure 5A:
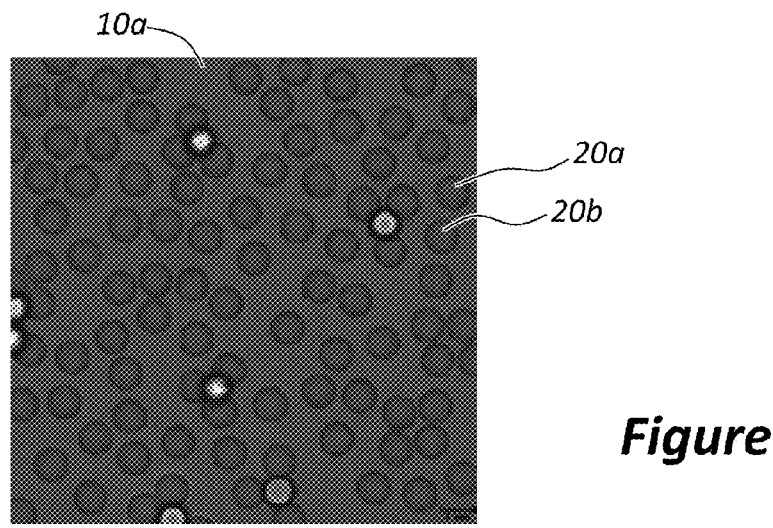
FIGS. 5a, 5b and 5c illustrate exemplary patterns of microsphere formation on a chemically charged glass substrate pursuant to the method disclosed.
Figure 5B:
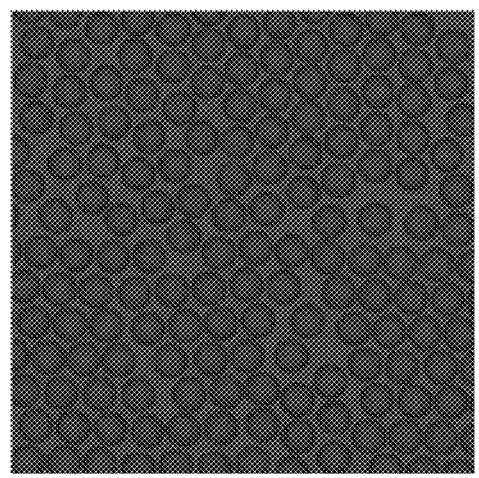
Figure 5C:
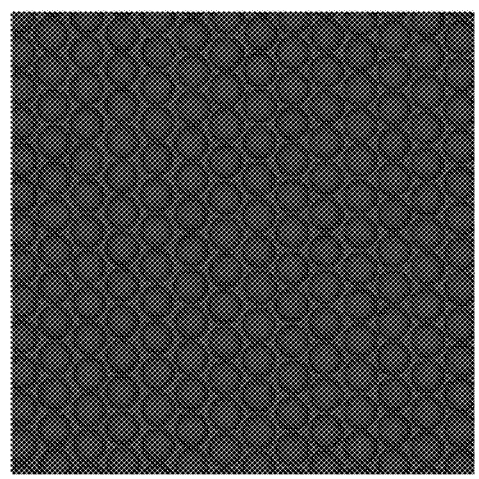

FIGS. 5a, 5b and 5c illustrate exemplary patterns of microsphere formation on chemically charged glass substrate pursuant to the method disclosed. FIGS. 5a through c illustrate exemplary patterns of particle formation on a glass substrate that is modified with a salt solution and by altering the temperature. In the exemplary embodiments shown, a glass substrate is modified with a polyelectrolyte salt solution wash to create charged attachment sites for PS microsphere immobilization. The particle formation is then transferred to the host polymer to form the monolayer.

FIGS. 5a through c illustrate exemplary Brightfield optical and illustrate how microsphere arrangement (e.g., particle density and interspacing) is affected by varying the polyelectrolyte salt solution concentrate and temperature. FIG. 5a illustrates miscrosphere formation using a 2.0 mol/L NaCl polyelectrolyte salt concentration at room temperature and exhibits nonplanar sporadic clustering typified by bright microspheres with dark halo formation positioned at variable focal distances. FIG. 5b shows a 1.0 mol/L NaCl polyelectrolyte salt concentration at room temperature showed no clustering and tighter particle packing. FIG. 5c shows the pattern formed by the 1.0 mol/L NaCl at a temperature of 70° C. At the inducing convective flux showed no clustering with hexagonal particle packing.

The 1.0 mol/L NaCl polyelectrolyte salt concentration sample shown in FIG. 5c exhibits a larger number of substrate-bound PS microspheres with the shorter interparticle spacing. Undesirable formations, including stacked or nonplanar clustering observed at higher salt concentrations are not observed at this modified lower salt concentration.

After the microsphere patterns have formed on the glass substrate, the viscous PDMS liquid is cast to anchor the microspheres in position on the glass-on-glass substrate and allowed to cure into an elastic solid. The cured elastomeric layer was delaminated to transfer the microspheres onto its surface.

As illustrated in FIGS. 5a, 5b and 5c particle transfer yield is higher as high polyelectrolyte salt concentration is increased. The increased salt solution may weaken bonding of the microspheres to the washed glass substrate, thereby facilitating ease of transfer to the elastomer.

In various embodiments, the inter-particle spacing may be further decreased by preheating the glass substrates to introduce thermal energy.

FIG. 6a through FIG. 6d illustrate various embodiments of surface profiles of microspheres within a monolayer. It is important to control axial position of the microspheres relative to the layer interfaces (axial layer position).

Axial resolution is critical to quantifying OCT resolution. The microspheres should have minimal deviation or protrusion from the monolayer surface.

Controlling axial direction allows for the stacked layers of particles and PDMS to have well-defined placement regardless of the lateral measurement location.

Figure 6A:
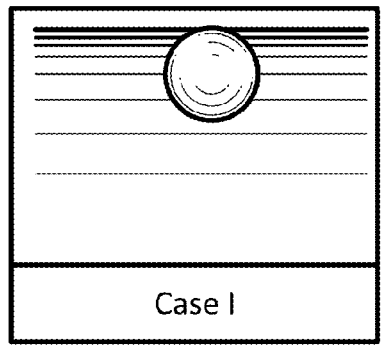
FIG. 6a through 6d illustrate exemplary embodiments of monolayers within a phantom test target structure which have varying axial distributions of microsphere axial.
Figure 6B:
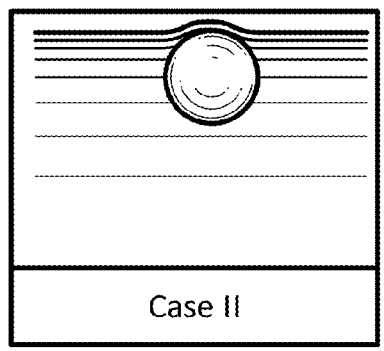
Figure 6C:
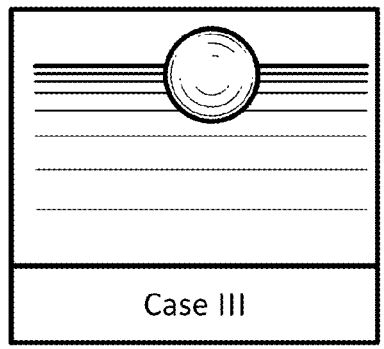
Figure 6D:
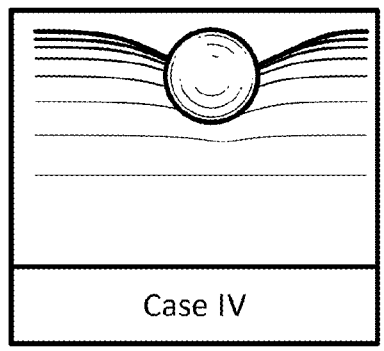

In FIG. 6a, the particle layer is completely buried within the PDMS matrix, with the top of the microsphere contacting the exposed surface. In FIG. 6a the microspheres are completely submerged in the polymer and subjacent to surface; in FIG. 6b, microspheres protrude from the surface with polymer coverage of microsphere. In FIG. 6c microspheres protrude from surface with no PDMS coverage of microsphere. In FIG. 6d sunken microspheres are submerged in the PDMS and protruding from surface.

In FIG. 6a, microspheres are completely submerged in the elastomer with an axial position directly subjacent to the polymer surface as a result of the delamination force required to detach the elastomer from glass. In FIG. 6b, the microspheres protrude slightly above the polymer surface represented particles protruding from the surface capped with a slight amount of the PDMS on top. In FIG. 6c, microsphere protrusions above the polymer surface are observed due to the smaller delamination force required to detach the elastomer from the glass substrate compared to that required to mechanically exfoliate the strong electrostatically stabilized particles from the PEM layer. The resultant partially embedded microspheres assumed a higher axial position relative to the polymer surface after trailing behind the polymer during the delamination step.

In various embodiments, due to surface tension effects, some microspheres may not be completely submerged in PDMS, and divots typified by a depressed halo surrounding a black hole may result. When using SWLI profilometry, regions of high curvature cannot be measured, so null data points may reflect positions that are unresolvable by the measurement technique. Since particles on a modified glass substrate were unresolvable on using SWLI profilometry, voids may appear which are indicative of exposed particles.

To mitigate these effects, the salt concentration used for modifying the glass substrate may be decreased.

FIG. 7a through FIG. 7d are plots of surface profilometry of PS-embedded elastomer constructs using varying salt concentrations, which illustrate that surface irregularities are increased as salt concentration is increased.

Figure 7A:
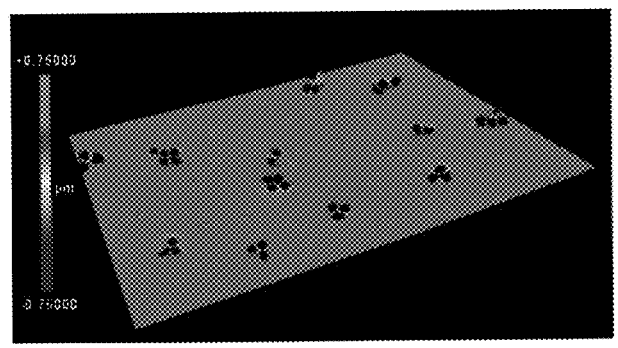
FIGS. 7a through 7h are plot diagrams which illustrate how the axial distribution of microspheres can be controlled by varying chemical treatment of the glass substrates.
Figure 7B:
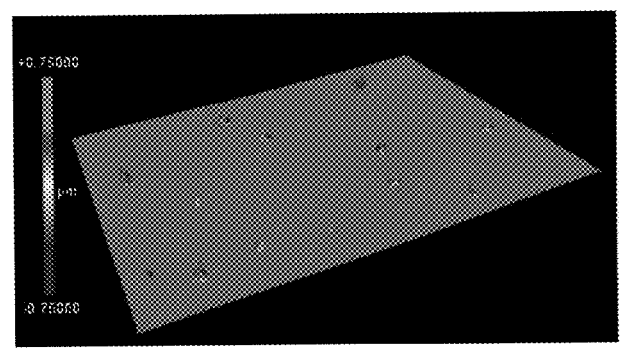
Figure 7C:
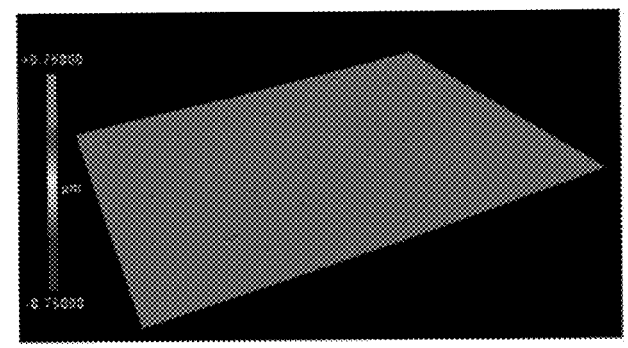
Figure 7D:
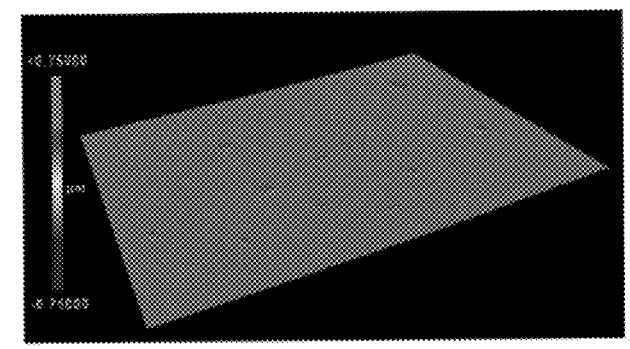
Figure 7E:
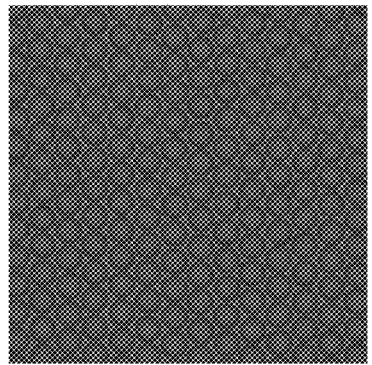
Figure 7G:
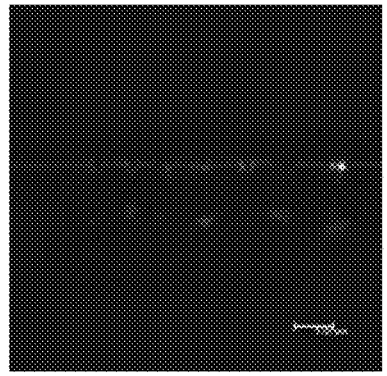
Figure 7F:
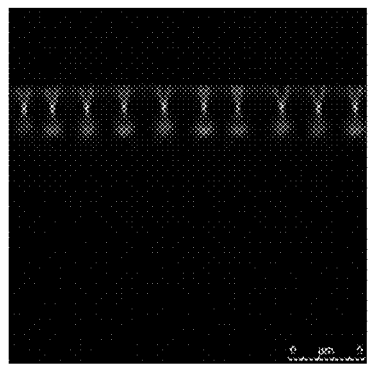
Figure 7H:
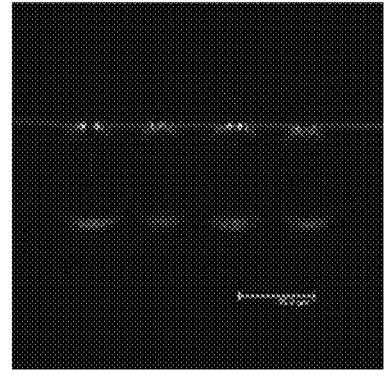

FIGS. 7f and 7g represent the confocal reflectance images of the microspheres (5 um and 10 um diameters, respectively) to illustrate relative planar axial positioning of microspheres subjacent to polymer surface profiled by FIGS. 7b-e.

Figure 8:
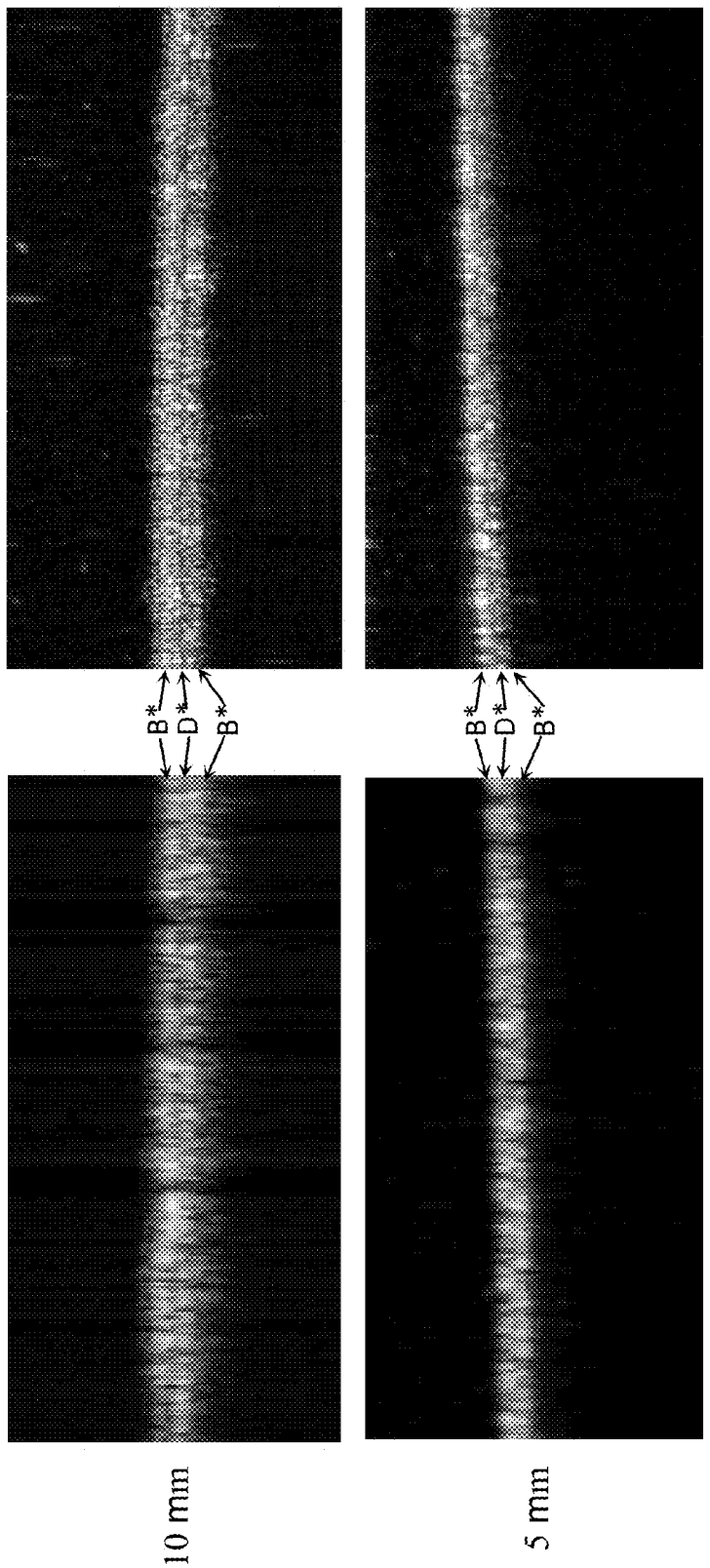
FIG. 8 illustrates an exemplary OCT images of a phantom test target structure to illustrate how a phantom test structure is used to calibrate a system under test.

FIG. 8 illustrates an OCT images of exemplary multilayered phantom test target produced a system under test.

In this exemplary embodiment, the theoretical axial resolution RoCT for these OCT imaging systems is given by the following relation:

$$R_{OCT} = \frac{l_c}{2} \approx 0.44 \frac{\lambda_0^2}{\Delta\lambda}$$

Where $l_c$ represents the coherence length, $\lambda 0$ is the source center wavelength and $\Delta\lambda$ is the source bandwidth. Therefore, the FDOCT system operated at a center wavelength of 855 nm with 56 nm FWHM spectral bandwidth has a theoretical axial resolution of ≈6 μm. The TDOCT system, operating at a center wavelength of 1315 nm with 53 nm FWHM spectral bandwidth, has a theoretical axial resolution of ≈14 μm. The layered phantoms in this exemplary embodiment do not demonstrate any surface specular reflections, because the layers of interest were buried ~1 mm beneath the top PDMS layer.

Figure 9:
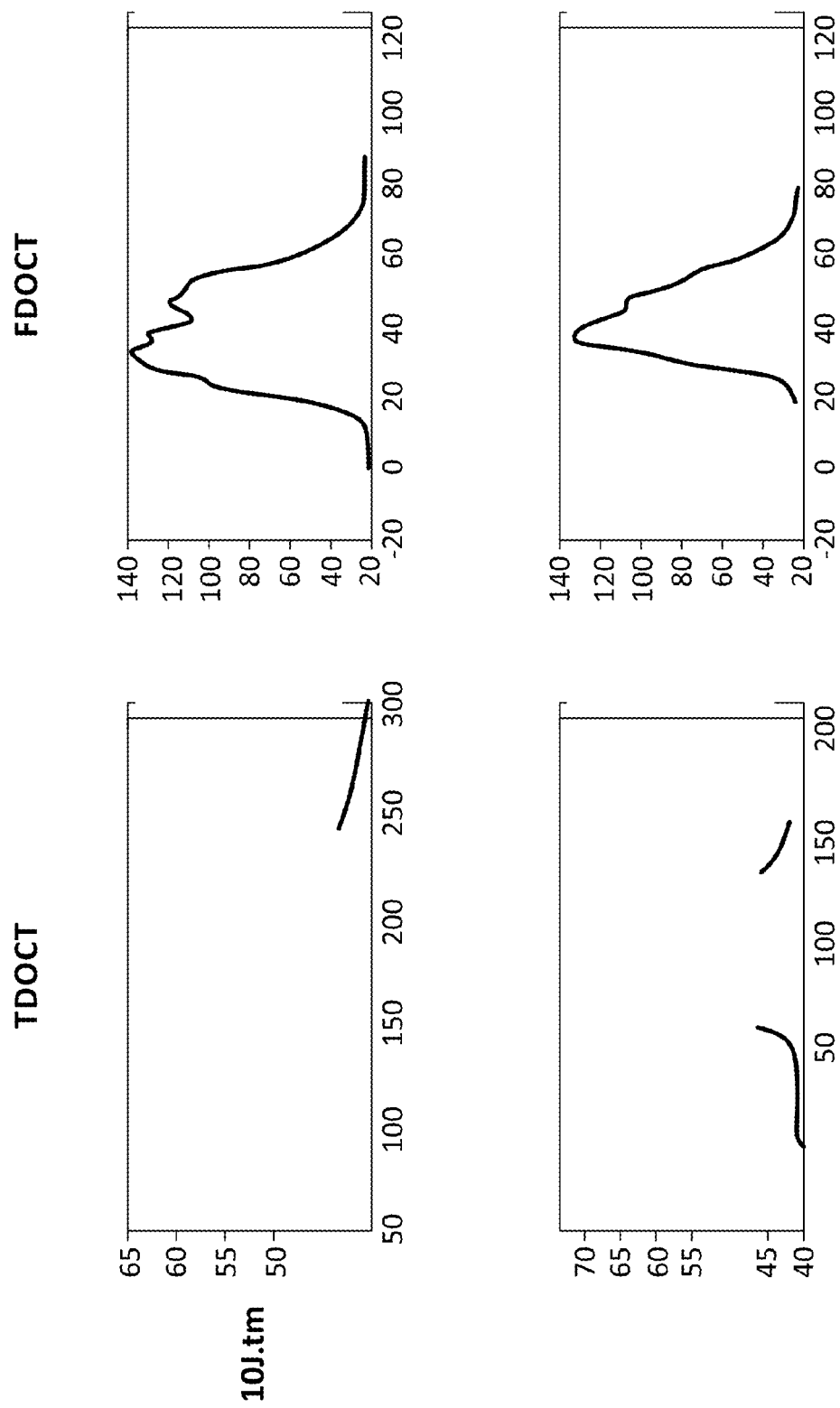
FIG. 9 illustrates axial intensity line scan plots for the acquired OCT images of a phantom test target structure.

FIG. 9 illustrates axial intensity line scan plots for the acquired OCT images of a phantom test target structure.

What is claimed is:

1. An optically uniform phantom test target structure comprised of:
   a plurality of micrometer scale monolayers wherein each micrometer scale monolayers is comprised of light-scattering microspheres suspended in a host polymer, wherein said light-scattering microspheres comprise an ordered monolayer array in each micrometer scale monolayer,
   a plurality of transparent polymer layers, wherein each transparent polymer layer is positioned between two of said micrometer scale monolayers;
   wherein at least one transparent polymer layer of said plurality of transparent polymer layers has a varying thickness from at least another transparent polymer layer of said plurality of transparent polymer layers;
   wherein said thicknesses of each of said plurality of transparent polymer layers are capable of being measured by an interferometer; and
   wherein said thickness of each transparent polymer layer of said plurality of transparent polymer layers replicates a different spatial frequency in the axial dimension of said phantom test target.

2. The phantom test target structure of claim 1 wherein said light-scattering microspheres do not substantially protrude above a surface of at least one of said plurality of monolayers sufficiently to alter the reflective characteristics of said light scattering microspheres.

3. The phantom test target structure of claim 1 which further includes axial dimensions which are determined independently of an optical system under test.

4. The phantom test target structure of claim 1 wherein each microsphere of said microspheres has wavelength-dependent scattering coefficients determined independently of an optical system under test.

5. The phantom test target structure of claim 1 wherein each microsphere of said microspheres has an absorption co-efficient determined independently of an optical system under test.

6. The phantom test target structure of claim 1 wherein each of said plurality of micrometer scale monolayers is an assembly of said light-scattering microspheres having a hexagonal packing.

7. The phantom test target structure of claim 6 wherein said ordered monolayer array of said light-scattering microspheres is formed by convective particle flux on a glass substrate.

8. The phantom test target structure of claim 1 wherein said optically uniform phantom test target structure is a calibration tool for axial resolution and contrast characterization.

9. The phantom test target structure of claim 1 which further comprises alternating micrometer scale monolayers with transparent polymer layers, wherein each of said micrometer scale monolayers and transparent polymer layers has a known thickness, wherein the periodicity of the repeating layers is known.

10. The phantom test target structure of claim 9 wherein said reflective layers have homogeneous scattering characteristics and appear optically uniformly bright in an image.

11. The phantom test target structure of claim 1 wherein said micrometer scale monolayers are arranged into a multilayered optical tissue phantom test target structure having spatial frequencies which correspond to a predetermined OCT illumination source coherence length.

12. The phantom test target structure of claim 1 wherein said host polymer is comprised of polydimethylsiloxane (PDMS) with a refractive index of 1.41 is used to embed polystyrene (PS) light-scattering microspheres with a contrasting refractive index.

13. The phantom test target structure of claim 1 wherein said microspheres have nominal diameters of either 5 μm or 10 μm and a refractive index of 1.57.

14. A method for producing the optically uniform phantom test structure of claim 1, comprised of the steps of:

electrically charging a glass substrate to form a modified glass substrate having a uniform electrical charge;

preparing an electrolyte solution to optimize particle substrate binding, wherein electrolyte solution is comprised of a aqueous solution;

treating a glass substrate with said electrolye solution;

axially positioning said microspheres on said substrate to provide a dense packing of microspheres;

delaminating said coating of microspheres to form a light scattering monolayer of microspheres;

combining said monolayers of microspheres into a multilayer test target structure by positioning polymer layers between said light-scattering monolayers of said light-scattering microsphere;

and measuring said surface of said monolayer with a profilometer capable of measuring step height changes over a range of 50 nm to 1 mm.

15. The method of claim 14 wherein said coating of said bed of charged polyelectrolyte multilayers (PEMs) is accomplished by using convective particle flux for two-dimensional crystal array formation on a glass substrate.

16. The method of claim 14 which further includes the step of utilizing layer-by-layer (LBL) polyelectrolyte deposition to optimize microsphere transfer from a glass substrate to said polyelectrolyte multilayers (PEMs) to form said microsphere monolayer.

17. The method of claim 14 which further includes a step of assembling a monolayer of polystyrene (PS) microspheres and transferring them into a polydimethylsiloxane (PDMS).

18. The method of claim 14 which further includes a step of dispersing PS microspheres into a scattering monolayer.

19. The method of claim 14 which further includes a step of successively dipping a plasma-treated glass substrate with several alternating charged bilayers of polyelectrolytes.

20. The method of claim 14 which further includes a step of selecting a charging solution selected from a group consisting of the polycation poly(allylamine hydrochloride) (PAH) and the polyanion poly(sodium 4-styrene sulfonate) (PSS).

* * * * *